US008467052B1

(12) United States Patent
Chao et al.

(10) Patent No.: US 8,467,052 B1
(45) Date of Patent: Jun. 18, 2013

(54) SYSTEMS AND METHODS FOR DETECTING CONTAMINANTS IN A SAMPLE

(75) Inventors: Kuanglin Chao, Ellicott City, MD (US);
Moon S. Kim, Silver Spring, MD (US);
Alan M. Lefcourt, Elkridge, MD (US);
David Tuschel, Monroeville, PA (US);
Oksana Olkhovyk, Pittsburgh, PA (US);
Yongliang Liu, Laurel, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 319 days.

(21) Appl. No.: 12/614,000

(22) Filed: Nov. 6, 2009

Related U.S. Application Data

(60) Provisional application No. 61/198,710, filed on Nov. 7, 2008.

(51) Int. Cl.
*G01J 3/44* (2006.01)
(52) U.S. Cl.
USPC .......................................................... 356/301
(58) Field of Classification Search
USPC ................................................. 356/300–318
See application file for complete search history.

(56) References Cited

U.S. PATENT DOCUMENTS

| 4,559,075 A | 12/1985 | Freepons | |
|---|---|---|---|
| 6,950,184 B2 * | 9/2005 | Stewart et al. | 356/301 |
| 2003/0030800 A1 * | 2/2003 | Golden et al. | 356/301 |
| 2006/0055923 A1 * | 3/2006 | Stewart et al. | 356/301 |

OTHER PUBLICATIONS

Anthony Kai-ching Hau et al. "Melamine Toxicity and the Kidney" 2009 Journal of American Society of Nephrology vol. 20, pp. 245-250.*
Gowen, A.A. et al., Hyperspectral Imaging-an Emerging Process Analytical Tool for Food Quality and Safety Control, Trends in Food Science & Technology, vol. 18, 2007, pp. 590-598.
Toray Industries Inc., "Flame-Resistant Polyamides, Japan Tokkyo Koko JP 8222348" Chem Abstracts (1982).
Schneider, J.R., and B. Schrader. "Measurement and Calculation of the Infrared and Raman Active Molecular and Lattice Vibrations of the Crystalline Melamine (1,3,5-Triamino-S-Triazine)" J. of Molecular Structure (1975) 29:1-14.
Ozaki, Y., "Raman Spectroscopy" In: Spectral Methods in Food Analysis (1999) 427-462 Marcel Dekker, New York—Ed: M.M. Massoba.
Tseng, C-H., C.K. Mann, and T.J. Vickers, "FT-Raman Determination of Melamine and Melamine Cyanurate in Nylon" Applied Spectroscopy (1994) 48:4 535-537.
Scheepers, M.L., J.M. Gelan, R.A. Carleer, P.J. Adriaensens and D.J. Vanderzande, "Investifation of melamine-formaldehyde cure by Fourier transform Raman Spectroscopy" Vibrational Spectroscopy (1993) 6:55-69.

* cited by examiner

*Primary Examiner* — Tara S Pajoohi Gomez
(74) *Attorney, Agent, or Firm* — John Fado; Robert D. Jones; Lesley Shaw

(57) ABSTRACT

System and method for determining the presence of a contaminant in a sample using Raman spectroscopic data. The sample may be food or feed and the contaminant may be melamine. The sample is illuminated with substantially monochromatic light to produce Raman scattered photons. The Raman scattered photons are collected to generate Raman spectroscopic data. The Raman spectroscopic data may comprise at least one of a Raman spectrum and a spatially accurate wavelength resolved Raman image. The Raman spectroscopic data is analyzed to determine the presence or absence of a contaminant in a sample. The concentration of the contaminant in the sample can also be determined by using a ratio algorithm.

30 Claims, 10 Drawing Sheets

SYSTEMS AND METHODS FOR DETECTING CONTAMINANTS IN A SAMPLE

RELATED APPLICATIONS

This application claims the benefit of U.S. Provisional Application No. 61/198,710, entitled "Systems and Methods for Detecting Contaminants in a Sample", filed on Nov. 7, 2008.

FIELD OF DISCLOSURE

The present disclosure relates generally to systems and methods for the detection of contaminants in a sample. More specifically, the present disclosure relates to systems and methods for determining the presence of contaminants in a sample using Raman spectroscopy and Raman chemical imaging. The present disclosure also provides for determining the concentration of contaminants found in a sample.

BACKGROUND

Since the end of March, 2007, an unknown number of cat and dog deaths have been attributed to the organic compound melamine. Melamine, a common industrial chemical, is often added to resins to improve flame resistance and has been proposed as an alternative form of fertilizer-N for plant growth. It was found that melamine was intentionally mixed with animal feed, in amounts ranging from 0.2% to 8% of total mass, as a way to boost the products' apparent protein content. Melamine was also used as a binder when making pellet feed for animals. As a result, the impact of melamine contaminated food and animal feed ingredients on food safety and animal health has become a major concern.

In addition to melamine, small amounts of cyanuric acid, ammeline, and ammelide were also detected in pet feed and in the tissue and urine of dead pets that consumed the contaminated food. Although it may be possible that cyanuric acid, ammeline, and ammelilde were added as contaminants, it is more likely that their presence in pet food resulted from the degraded derivatives of melamine.

There is great concern that melamine could again enter the food/feed chain and would be consumed by humans and animals. As part of the Food Protection Plan, US federal agencies, such as the USDA's FSIS and FDA, and other organizations have established the GC-MS and LC-MS/MS procedures for the analysis of melamine in food/feed commodities. Although they might be able to detect melamine contaminant in trace amounts, these time-consuming in-vitro procedures require chemical solvents for the extraction steps and depend on mass spectrometry which is expensive, time-consuming, and labor-intensive.

There exists a need for rapid, non-destructive, specific, low-cost, and routine systems and methods for the detection of melamine. Fast melamine screening requires minimal sample preparation (e.g., no extraction/centrifugation), routine analysis of a number of samples without reagents, minimal procedures and ease of operation. Such systems and methods are increasingly important because of the potential public and animal health concerns. In addition, systems and methods are needed for melamine screening to prevent protein fraud.

SUMMARY

The systems and methods of the present disclosure overcome the limitations of the prior art and provide for the rapid, accurate, non-destructive, specific, and routine screening of the presence of melamine in food and feed for public and animal safety and security. The present disclosure provides for the use of Raman spectroscopy and Raman chemical imaging to detect the presence and concentration of melamine and other contaminants in a sample.

When light interacts with matter, a portion of the incident photons are scattered in all directions. A small fraction of the scattered radiation differs in frequency (wavelength) from the illuminating light. If the incident light is monochromatic (single wavelength) as it is when using a laser source or other sufficiently monochromatic light source, the scattered light which differs in frequency may be distinguished from the light scattered which has the same frequency as the incident light. Furthermore, frequencies of the scattered light are unique to the molecular or crystal species present. This phenomenon is known as the Raman Effect.

In Raman spectroscopy, energy levels of molecules are probed by monitoring the frequency shifts present in scattered light. A typical experiment consists of a monochromatic light source (usually a laser) that is directed at a sample. Several phenomena then occur including Raman scattering which is monitored using instrumentation such as a spectrometer and a charge-coupled device (CCD). Similar to an infrared spectrum, a Raman spectrum reveals the molecular composition of materials, including the specific functional groups present in organic and inorganic molecules and specific vibrations in crystals. Raman spectrum analysis is useful because each resonance exhibits a characteristic 'fingerprint' spectrum, subject to various selection rules. Peak shape, peak position and the adherence to selection rules can also be used to determine molecular conformation information (crystalline phase, degree of order, strain, grain size, etc.). Unlike infrared spectroscopy, a single Raman spectrometer can be applied to the molecular characterization of organic and inorganic materials simultaneously. Other advantages of Raman over traditional infrared spectroscopy include the ability to analyze aqueous phase materials and the ability to analyze materials with little or no sample preparation.

In many respects, Raman chemical imaging is an extension of Raman spectroscopy. Raman chemical imaging combines Raman spectroscopy and digital imaging for the molecular-specific analysis of materials. Raman chemical imaging is a versatile technique that is well suited to the analysis of complex heterogeneous materials. In a typical experiment, a specimen is illuminated with monochromatic light, and the Raman scattered light is filtered by a spectrometer which passes only a single wavelength range. The Raman scattered light may then be used to form an image of the specimen. A spectrum is generated corresponding to millions of spatial locations at the sample surface by tuning an imaging spectrometer over a range of wavelengths and collecting images intermittently. Changing the selected passband (wavelength) of the imaging spectrometer to another appropriate wavelength causes a different material to become visible. A series of such images can then uniquely identify constituent materials, and computer analysis of the image is used to produce a composite image highlighting the information desired. Although Raman chemical imaging is predominately a surface technique, depth-related information can also be obtained by using different excitation wavelengths or by capturing chemical images at incremental planes of focus. Contrast is generated in the images based on the relative amounts of Raman scatter or other optical phenomena such as luminescence that is generated by the different species located throughout the sample. Since a spectrum is generated for each pixel location, chemometric analysis tools such as correlation analysis, Principle Component Analysis (PCA) and factor rotation, including Multivariate Curve Resolution (MCR) can be applied to the image data to extract pertinent information otherwise missed by ordinary univariate measures. A spatial resolving power of approximately 250 nm has been demonstrated for Raman chemical imaging using visible laser wavelengths. This is almost two orders of magnitude better than infrared imaging which is typically limited to 20 microns due to diffraction. In addition, image definition (based on the total number of imaging pixels) can be very high for Raman chemical imaging because of the use of high pixel density detectors (often 1 million plus detector elements).

DETAILED DESCRIPTION OF THE DISCLOSURE

Reference will now be made in detail to the embodiments of the present disclosure, examples of which are illustrated in the accompanying drawings. Wherever possible, the same reference numbers will be used throughout to refer to the same or like parts.

Figure 1:
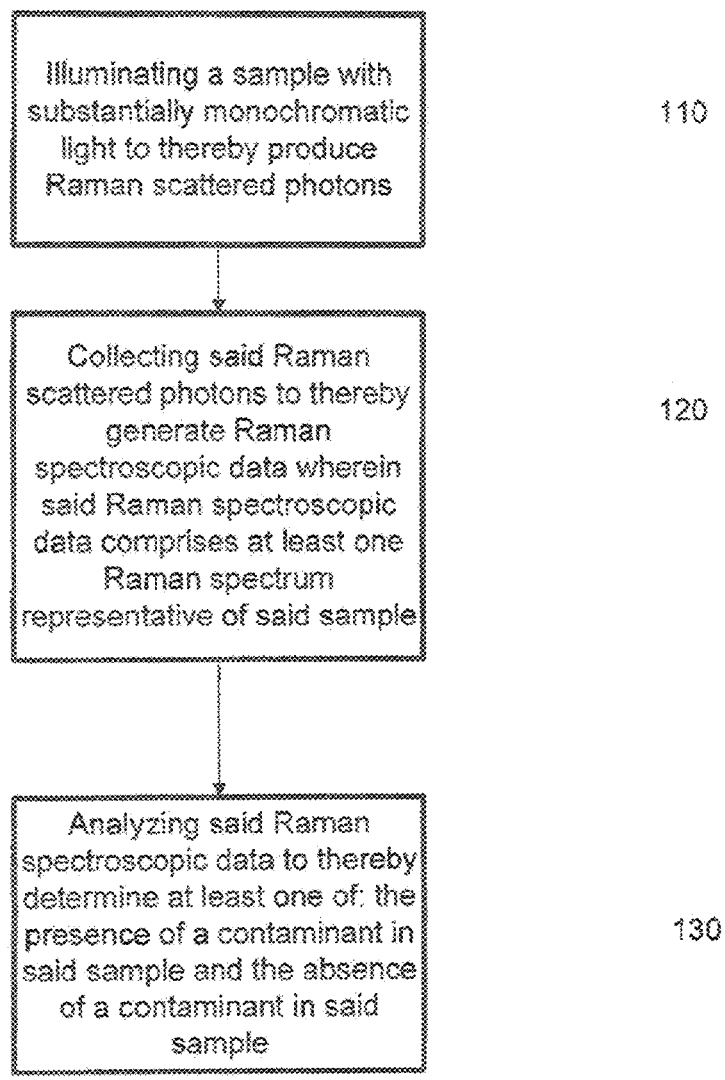
FIG. 1 is illustrative of one method of the present disclosure.

The present disclosure provides for systems and methods for detecting the presence and concentration of various contaminants, including melamine. In one embodiment, illustrated by FIG. 1, the present disclosure provides for a method 100. In step 110, a sample is illuminated with substantially monochromatic light to thereby produce Raman scattered photons. In step 120, said Raman scattered photons are collected to thereby generate Raman spectroscopic data wherein said Raman spectroscopic data comprises at least one Raman spectrum. In step 130 said Raman spectroscopic data is analyzed to thereby determine at least one of: the presence of a contaminant in the sample and the absence of a contaminant in the sample.

The sample may comprise any food or feed known in the art including but not limited to human or animal food or feed. Non-limiting examples of samples contemplated by the present disclosure include: wheat, flour, corn gluten, and soybean meal, among others known in the art and combinations thereof.

The contaminant of interest may be any known in the art and combinations and derivatives thereof. The contaminant may be any substance or material that renders the sample harmful, toxic, unsuitable, impure, or unusable. In one embodiment, the contaminant comprises at least one of melamine, cynuric acid, ammeline, and ammelide.

In one embodiment, the sample is illuminated using widefield illumination in which the entire field of view to be investigated is illuminated simultaneously. In such an embodiment, Raman scattered light is obtained from each point within the field of view simultaneously. In another embodiment, the sample is illuminated using a 1064 nm excitation laser in the near-infrared (NIR) region. In yet another embodiment, the sample is illuminated using a 785 nm excitation laser. In one embodiment, a Raman spectrum representative of the sample comprises a peak (Raman band) at approximately 670 cm$^{-1}$. This can be used to determine the presence or absence of a contaminant in the sample.

In one method of the present disclosure, collected photons are passed though a filter. The filter may comprise a tunable filter selected from the group including but not limited to: Liquid Crystal Tunable Filter (LCTF), Acousto-Optic Tunable Filter (AOTF), and Multi Conjugate Filter (MCF).

It is contemplated by the present disclosure that any number of Raman spectra representative of the sample can be obtained for analysis and/or comparison. In one embodiment, the method may further comprise applying a ratio algorithm to determine the concentration of a contaminant present in the sample. In one embodiment, the concentration of the contaminant will constitute at least 0.2% of the total weight of the sample. However, it is contemplated that the systems and methods disclosed herein can be used to determine other concentrations of the contaminant in a sample.

In another embodiment, the method may further comprise obtaining a spatially accurate wavelength resolved Raman image representative of said sample. The spatially accurate wavelength resolved Raman image can then be analyzed to determine the presence or absence of a contaminant in the sample and the concentration of any such contaminant.

Figure 2:
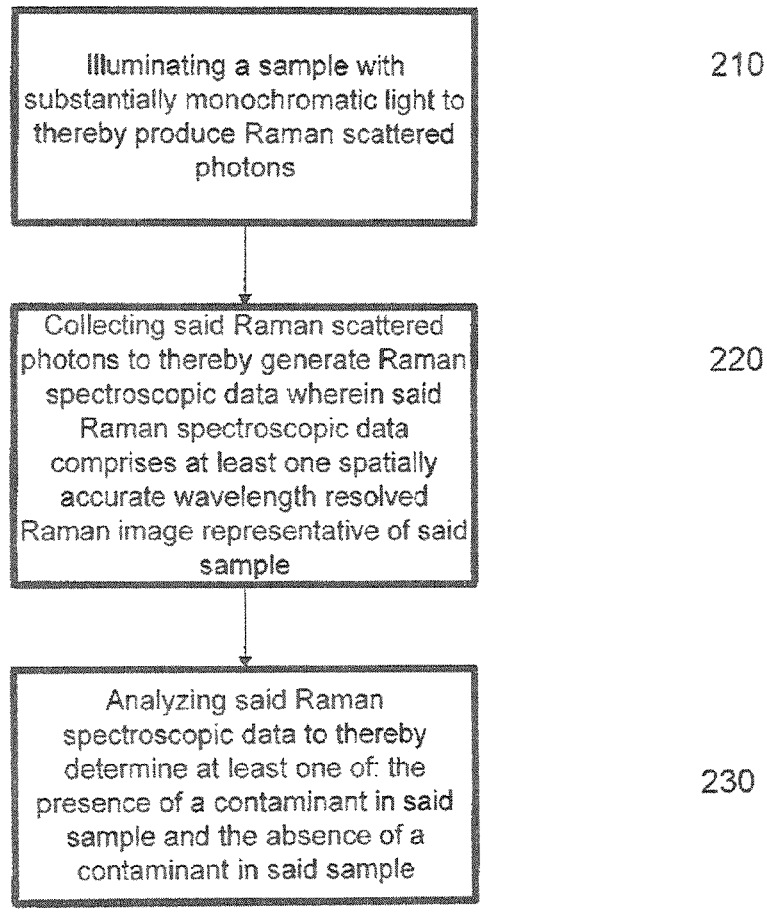
FIG. 2 is illustrative of one method of the present disclosure.

In another embodiment, illustrated by FIG. 2, the present disclosure provides for a method 200. In step 210, a sample is illuminated with substantially monochromatic light to thereby produce Raman scattered photons. In step 220, said Raman scattered photons are collected to thereby generate Raman spectroscopic data wherein said Raman spectroscopic data comprises at least one spatially accurate wavelength resolved Raman image. In step 230, said Raman spectroscopic data is analyzed to thereby determine at least one of: the presence of a contaminant in a sample and the absence of a contaminant in a sample.

In another embodiment, the method may further comprise obtaining at least one Raman spectra representative of said sample. The Raman spectra can then be analyzed to determine the presence or absence of a contaminant in the sample and the concentration of any such contaminant. It is also contemplated by this disclosure that the method can be performed on a macroscopic scale.

In another embodiment, the method may further comprise obtaining a bright field image representative of the sample. The bright field image may be obtained by illuminating the sample with broadband light to thereby produce photons reflected, absorbed, scattered or transmitted by the sample. These photons are then collected to form at least one bright field image representative of the sample. The bright field image is fused with the spatially accurate wavelength resolved image and a region of interest of the sample can be obtained. In one embodiment, the images are fused using software that may be ChemImage Xpert™ software available from ChemImage Corporation, Pittsburgh, Pa., U.S.A. The region of interest may be a region suspected to contain a contaminant or suspected to be void of a contaminant. At least one Raman spectrum representative of the region of interest is obtained. The Raman spectrum is analyzed to determine the presence or absence of a contaminant in the sample. It is contemplated by the present disclosure that any number of regions of interest may be identified and the associated Raman spectra obtained.

Figure 3:
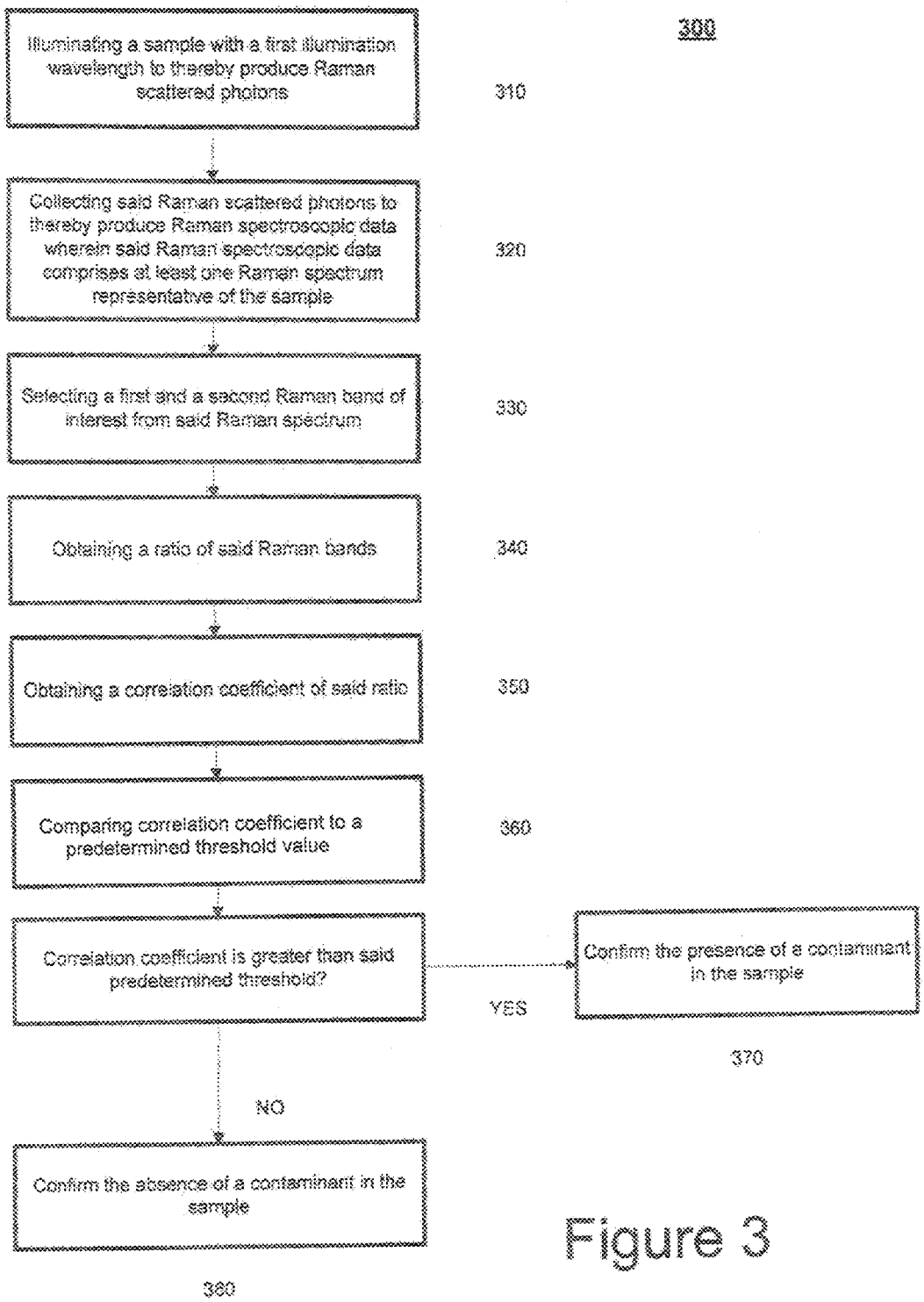
FIG. 3 is illustrative of one method of the present disclosure.

FIG. 3 illustrates one method 300 that can be used to determine the presence of and concentration of a contaminant. In step 310, a sample is illuminated with a first illumination wavelength to thereby produce Raman scattered photons. In step 320 the Raman scattered photons are collected to thereby generate Raman spectroscopic data wherein said Raman spectroscopic data comprises at least one Raman spectrum representative of said sample. In step 330, a first and a second Raman band of interest is selected from said Raman spectrum. A ratio of the Raman bands is obtained in step 340. In step 350 a correlation coefficient of said ratio is obtained. In step 360 the correlation coefficient is compared to a predetermined threshold value. If the correlation coefficient is greater than the predetermined threshold, the presence of a contaminant in the sample is confirmed in step 370. If the correlation coefficient is less than the predetermined threshold, the absence of a contaminant in the sample is confirmed in step 380.

The present disclosure also provides for a system for detecting the presence of a contaminant in a sample. In one embodiment, the system comprises: an illumination source configured to illuminate a sample with substantially monochromatic light to thereby produce Raman scattered photons, a detector for detecting said Raman scattered photons and generating Raman spectroscopic data representative of said sample, a processor for processing said Raman spectroscopic data representative of said sample, and a display for displaying at least one of a Raman spectrum representative of said sample and a spatially accurate wavelength resolved Raman image representative of said sample. In one embodiment, the illumination source is an excitation laser selected from the group consisting of 785 nm and 1064 nm. In another embodiment, the illumination source is a Nd:YAG excitation laser. The Nd:YAG excitation laser can be configured to comprise a 1064 nm excitation laser. In one embodiment, the system further comprises a filter for filtering said Raman scattered photons. The filter may be a tunable filter selected from the group consisting of but not limited to: Liquid Crystal Tunable Filter (LCTF), Acousto-Optic Tunable Filter (AOTF), and Multi Conjugate Filter (MCF). In one embodiment, the system of the present disclosure the detector is an InGaAs detector.

Figure 4:
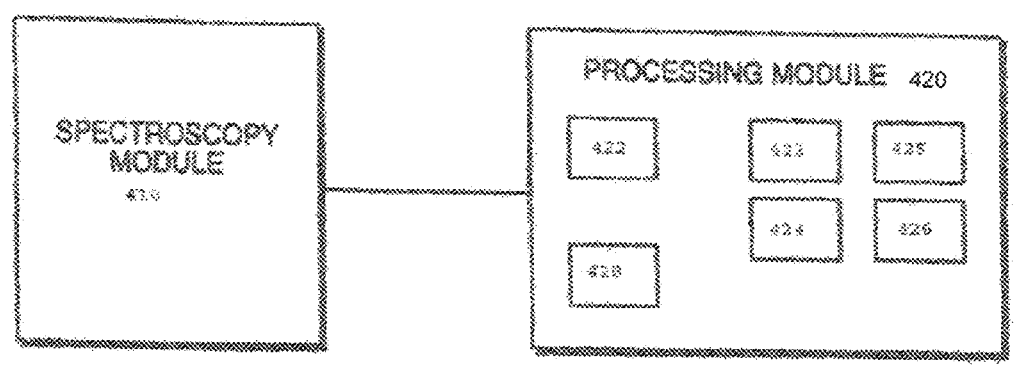
FIG. 4 is representative of a system of the present disclosure.

FIG. 4 illustrates an exemplary system 400 according to one embodiment of the present disclosure. System 400 includes a spectroscopy module 410 in communication with a processing module 420. Processing module 420 may include a processor 422, databases 423, 424, 425 and 426, and machine readable program code 428. The machine readable program code 428 may contain executable program instructions, and the processor 422 may be configured to execute the machine readable program code 428 so as to perform the methods of the present disclosure. In one embodiment, the program code 428 may contain the ChemImage Xpert™ software marketed by ChemImage Corporation of Pittsburgh, Pa. The Xpert™ software may be used to process spectroscopic data and information received from the spectroscopy module 410 to obtain various spectral plots and images, and to also carry out various multivariate image analysis methods discussed later herein below.

Figure 5A:
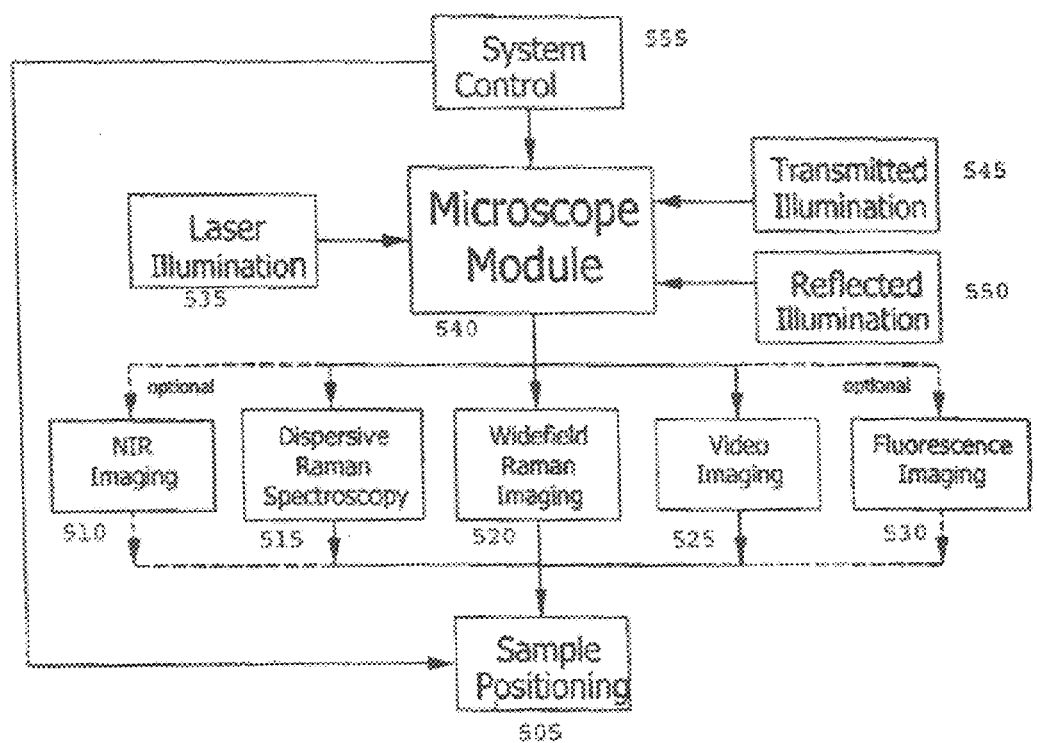
FIGS. 5A and 5B are representative of a system of the present disclosure.

FIG. 5A illustrates an exemplary schematic layout of the spectroscopy module 410 shown in FIG. 4. The layout in FIG. 5A may relate to the Falcon II™ Raman Chemical Imaging system marketed by ChemImage Corporation of Pittsburgh, Pa. In one embodiment, the spectroscopy module 410 may include a microscope module 540 containing optics for microscope applications. An illumination source 535 (e.g., a laser illumination source) may provide illuminating photons to a sample (not shown) handled by a sample positioning unit 505 via the microscope module 540. In one embodiment, photons transmitted, reflected, emitted, or scattered from the illuminated sample (not shown) may pass through the microscope module before being directed to one or more of spectroscopy or imaging optics in the spectroscopy module 410. In the embodiment of FIG. 5A, dispersive Raman spectroscopy 515, wide-field Raman imaging 520, and bright field video imaging 525 are illustrated as "standard" operational modes of the spectroscopy module 410. Two optional imaging modes—fluorescence imaging 530 and NIR (Near Infrared) imaging 510—may also be provided if desired. The spectroscopy module 410 may also include a control unit 460 to control operational aspects (e.g., focusing, sample placement, laser beam transmission, etc.) of various system components including, for example, the microscope module 440 and the sample positioning unit 444 as illustrated in FIG. 5A. In one embodiment, operation of various components (including the control unit 555) in the spectroscopy module 410 may be fully automated or partially automated, under user control.

It is noted here that in the discussion herein the terms "illumination," "illuminating," "irradiation," and "excitation" are used interchangeably as can be evident from the context. For example, the terms "illumination source," "light source," and "excitation source" are used interchangeably. Similarly, the terms "illuminating photons" and "excitation photons" are also used interchangeably. Furthermore, although the discussion hereinbelow focuses more on Raman spectroscopy and Raman molecular imaging, various methodologies discussed herein may be adapted to be used in conjunction with other types of spectroscopy applications as can be evident to one skilled in the art based on the discussion provided herein.

Figure 5B:
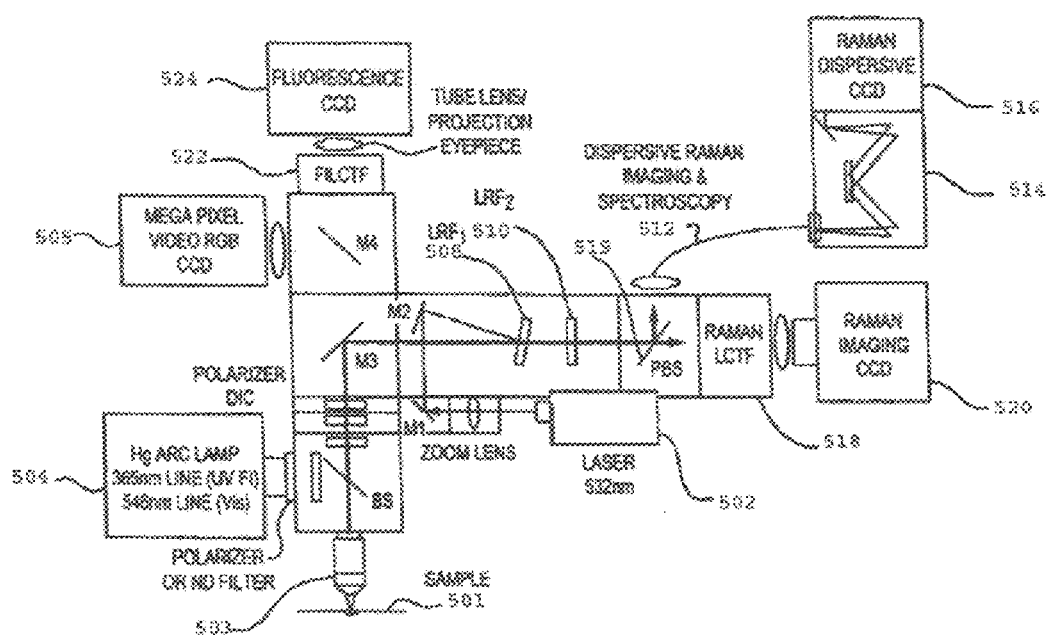

FIG. 5B illustrates exemplary details of the spectroscopy module 410 in FIG. 5A according to one embodiment of the present disclosure. Spectroscopy module 410 may operate in several experimental modes of operation including bright field reflectance and transmission imaging, polarized light imaging, differential interference contrast (DIC) imaging, UV induced autofluorescence imaging, NIR imaging, wide field illumination whole field Raman spectroscopy, wide field spectral fluorescence imaging, and wide field spectral Raman imaging. Module 410 may include collection optics 503, light sources 502 and 504, and a plurality of spectral information processing devices including, for example: a tunable fluorescence filter 522, a tunable Raman filter 518, a dispersive spectrometer 514, a plurality of detectors including a fluorescence detector 524, and Raman detectors 516 and 520, a fiber array spectral translator ("FAST") device 512, filters 508 and 510 and a polarized beam splitter (PBS) 519. In one embodiment, the processor 422 (FIG. 4) may be operatively coupled to light sources 502 and 504, and the plurality of spectral information processing devices 514, 518 and 522. In another embodiment, the processor 522 (FIG. 4), when suitably programmed, can configure various functional parts of the spectroscopy module in FIG. 4 and may also control their operation at run time. The processor, when suitably programmed, may also facilitate various remote data transfer and analysis operations. Module 410 may optionally include a video camera 505 for video imaging applications. Although not shown in FIG. 5, spectroscopy module 410 may include many additional optical and electrical components to carry out various spectroscopy and imaging applications supported thereby.

Examples: Melamine (>99+%) was purchased from Sigma-Aldrich Co, and used without further purification. Dry food/feed materials (wheat flour, corn gluten, and soybean meal) were obtained either from a local grocery store or from USDA's dairy center in Beltsville, Md., and all were used as received. Disposable glass tubes (6 mm in outside diameter× 50 mm in length) were supplied by Fisher Scientific (Suwanee, Ga., USA).

At least five (5) mixtures were prepared by mixing melamine contaminant and individual dry food/feed, with the amount of contaminants (w/w) in the range of 0.2, 0.5, 1.0, 3.0, and 6.0%. A mortar and pestle were used to obtain homogenous mixtures.

FT-Raman spectra were acquired on a FT-Raman module for a Nicolet 670 FT-IR bench (Madison, Wis., USA) using an InGaAs detector and XT-KBr beamsplitter. The glass tubes containing samples were illuminated using the Nd:YAG excitation laser operating at 1064 nm. Raman scattered light was accumulated using a 180° reflective mode with 0.5 W of laser power and 256 scans at 8 $cm^{-1}$ resolution. Three measurements were taken for each mixture. All spectra were transformed into .spc files (Grams file format) and then were smoothed with the Savitzky-Golay function of 2 polynomial and 11 points by the use of Grams/32 software (Version 7.0, Galactic Industries Corp., Salem, N.H., USA). The data set was loaded into Microsoft Excel 2000 to execute a simple algorithm analysis.

Figure 6:
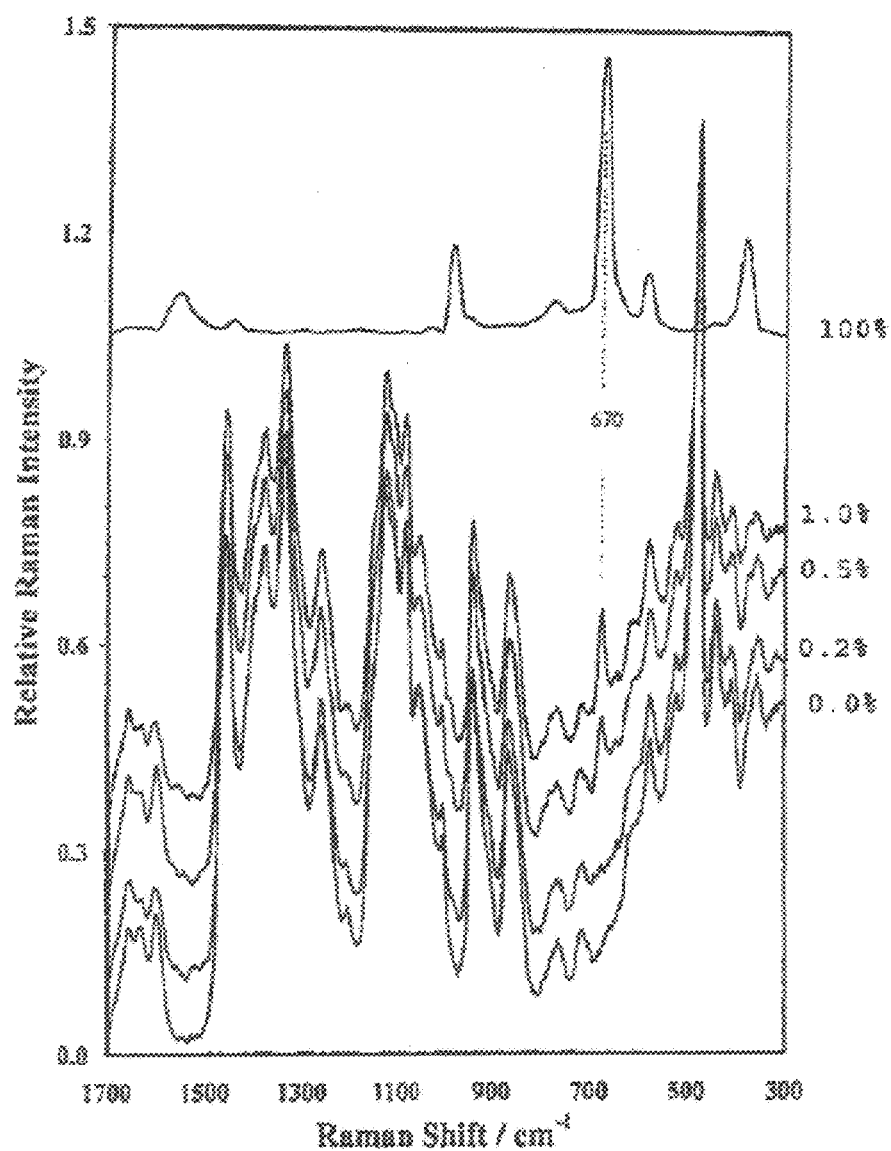
FIG. 6 shows representative FT-Raman spectra of melamine contaminated wheat flours at percentages (%, w/w) of 0 (pure wheat flour), 0.2, 0.5, 1.0 and 100 (pure melamine), from top to bottom. Raman intensity of melamine was scaled and all spectra were shifted vertically for direct comparison.

FIG. 6 shows the representative melamine concentration-dependent FT-Raman spectra of melamine and wheat flour mixture at melamine percentages (% w/w) of 0, 0.2, 0.5, 1.0 and 100 in the 1700-300 $cm^{-1}$ region. It indicates that melamine and wheat flour have unique Raman bands which increase or decrease in intensity with the relative amount of melamine. A dominant melamine Raman band at 670 $cm^{-1}$ was of much interest because it was the strongest one and also was well separated from those ascribed to wheat flour. This intense melamine band arises from the breathing mode of the triazine ring. Careful comparison of spectra in FIG. 6 suggested that there exists a weak 670 $cm^{-1}$ band in the spectrum of the mixture containing 0.2% melamine, and the intensity increased with the melamine amount. Therefore, the 670 $cm^{-1}$ band could surprisingly be used to identify the presence of a melamine component as low as a 0.2% level in wheat flour.

Figure 7:
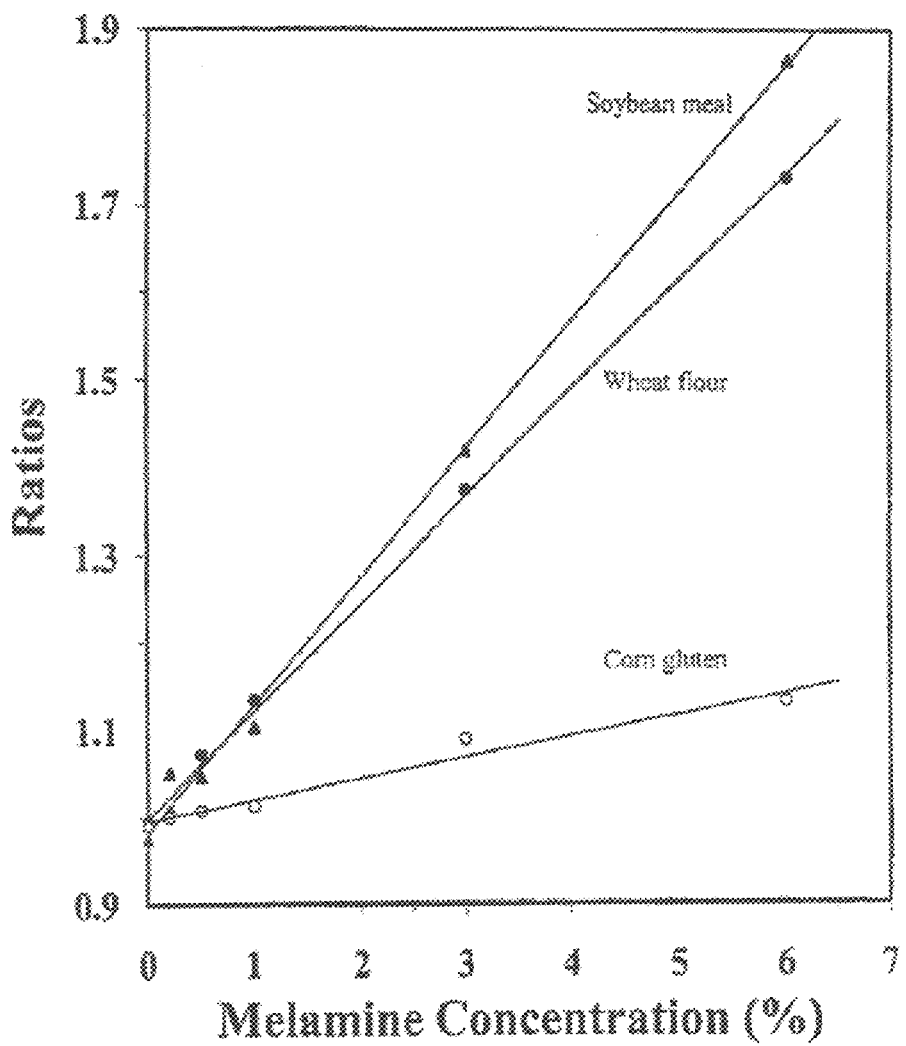
FIG. 7 shows the relationship between the intensity ratio and melamine concentration in wheat flour (•), corn gluten (○), and soybean meal (▲). Each data point was the average of ratios from three spectral measurements.

In addition to determining whether melamine was present, it was of interest to assess its amount from a simple Raman measurement. FIG. 7 depicts the melamine amount-dependent band ratio of $I_{670}/I_{655}$, by using the Raman intensity at 670 $cm^{-1}$ against one at 655 $cm^{-1}$. In general, the ratio yielded a nearly linear relationship with a correlation coefficient ($R^2$) of 0.99.

Figure 8:
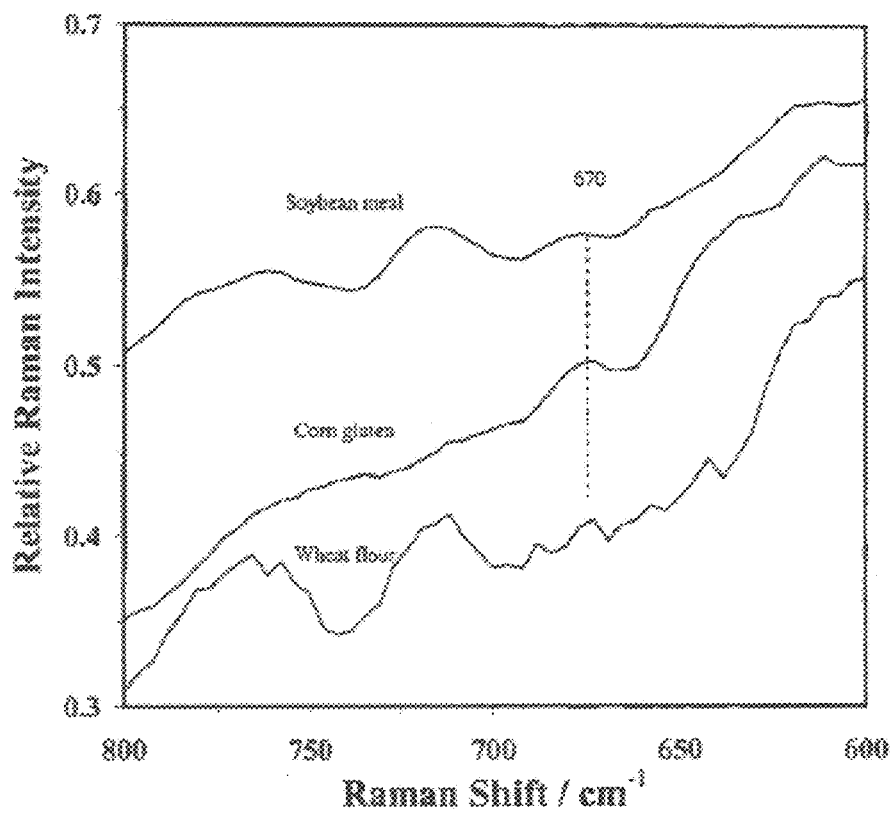
FIG. 8 shows typical FT-Raman spectra of melamine contaminated wheat flours, corn gluten, and soybean meal at the percentage of 0.2%. All spectra were shifted vertically for direct comparison.

Mixtures of melamine added into dry food/feed materials, such as corn gluten and soybean meal, were prepared in the same way as for the wheat flour mixtures. FT-Raman spectra of melamine-concentrated corn gluten and soybean meal revealed the distinctive 670 $cm^{-1}$ band, whose intensity increased as expected with increasing melamine concentration. For comparison, FT-Raman spectra of three mixtures containing 0.2% melamine are given in FIG. 8. Due to large variations in chemical/ingredient constituents and color among wheat flour, corn gluten, and soybean meal, the differences observed in relative intensity and position of Raman bands were reasonable. Notably, the Raman bands near 670 $cm^{-1}$ in the three mixtures were easily identifiable. Therefore, the dominant and well-isolated melamine band at 670 $cm^{-1}$ could surprisingly be used as a marker to detect the existence of melamine in the food/feed materials at levels as low as 0.2%.

Ratio values for melamine-contaminated corn gluten and soybean meal were also obtained and are plotted in FIG. 7. It can be seen that the ratio values were nearly linear with melamine concentration in the range of 0-6.0%, which correlation coefficients ($R^2$) of 0.99, 0.96, and 0.99 for wheat flour, corn gluten, and soybean meal, respectively.

Comparison of ratio values shown in FIG. 7 indicated a large discrepancy, and such a distinction could reflect the chemical, physical, and structural differences of the three food/feed materials. However, careful examination of the ratio values revealed that all uncontaminated samples (no melamine added) had ratio values less than 1.0. This was true for all three feed sample types—soybean meal, wheat flour, and corn gluten. Hence it could surprisingly be used as a universal value to identify melamine-contaminated materials from uncontaminated ones, even if the exact types of bulk materials are unknown.

Global-illumination (or wide-field) spectroscopic imaging was investigated. This technique combines spatially and spectrally resolved information about molecular identities of mixtures, in order to obtain non-invasive and highly reliable sensing of melamine. Raman chemical imaging (RCI) was used to access the feasibility of imaging the melamine particles in wheat flour. A 785 nm laser was used as the excitation source. The Raman scattering of melamine in wheat flour was collected through an electronically tuned liquid crystalline tunable filter (LCTF) over the spectral range from 610 $cm^{-1}$ to 1040 $cm^{-1}$ using 4 $cm^{-1}$ steps with a 5 second integration per wavelength frame. This narrow spectral range was chosen to detect the specific melamine triazine ring breathing mode. The resulting image presented a hyperspectral datacube possessing both spatial and spectral information.

Figure 9:
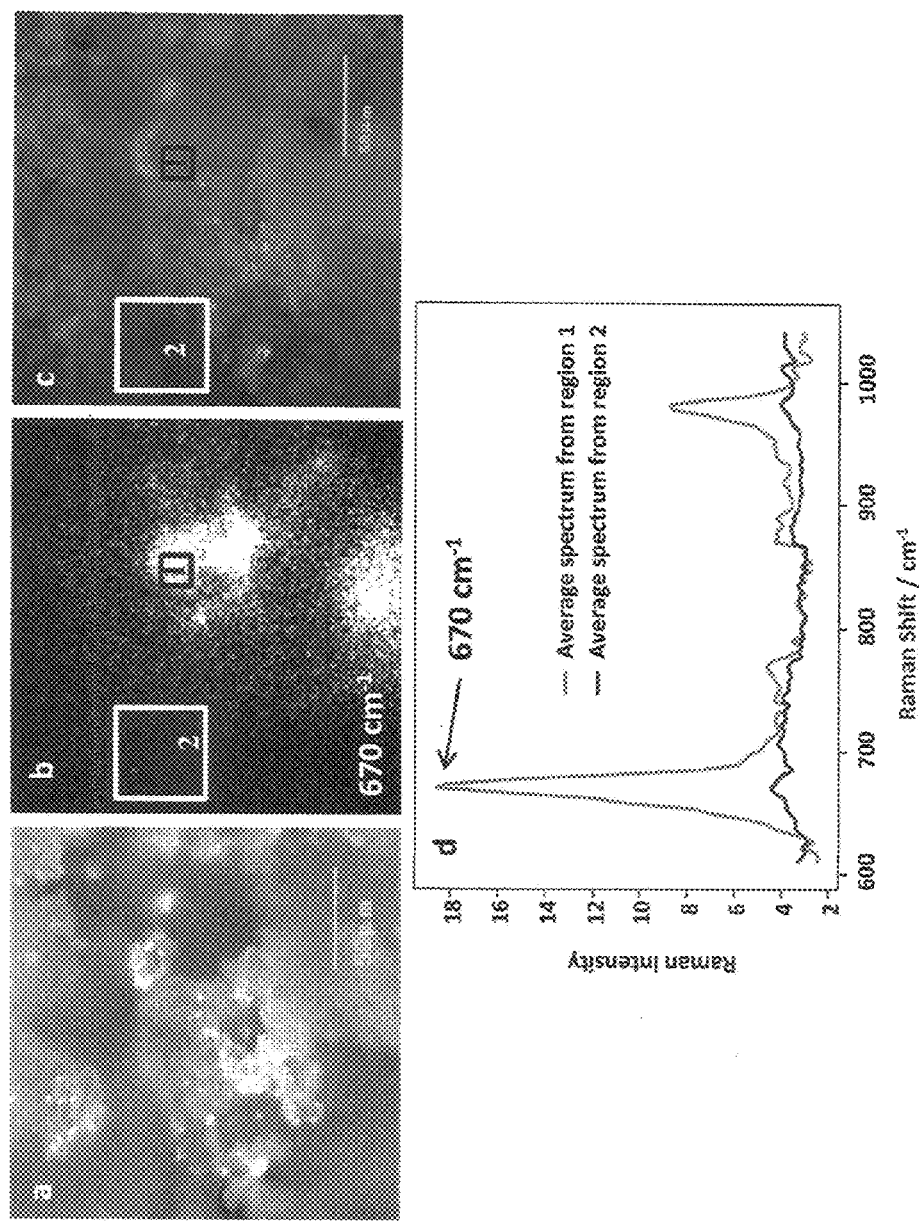
FIG. 9 shows bright field reflection image (a), corresponding Raman chemical image at 670 cm-1 (b), fusion of false-colored Raman chemical image with the corresponding bright field reflection image (c) and image-spectrometer-derived spectra of selected regions imaged (d) of a sample containing 6% wt mixture of melamine in wheat flour. Raman chemical image was obtained on ChemImage Raman Imaging system equipped with 785 nm laser excitation. Laser power at the laser head for the 785 nm excitation using a 10× objective was measured to be approximately 460 mW. Melamine in wheat flour mixture sample was prepared, characterized and supplied to ChemImage by USDA-ARS.

FIG. 9 shows a bright field reflection image of the wheat flour sample known to contain 6% melamine by weight. There was no noticeable heterogeneity in the bright field reflection image that can be attributed to the melamine contaminant. A Raman chemical image was collected on the same field of view as is shown in FIG. 9B where each pixel of the Raman chemical image had an associated Raman spectrum. Spectra from neighboring pixels that showed negative contrast at the frame of interest indicated chemical-specific spatial heterogeneity of the sample studied. FIG. 9D shows two spectra derived from the two regions in the Raman chemical image in FIG. 9B. FIG. 9C represents a bright field/Raman fusion image which combined the image information shown in FIGS. 9A and 9B where the melamine regions are shown in region 1 and the wheat flour regions are shown in region 2.

The study presented the surprising usefulness of the FT-Raman technique for the screening of contaminants (e.g., melamine) in food-feed products. The characteristic melamine Raman band near 670 cm$^{-1}$ was observed to be intense and well-separated from other bands attributed to food/feed components. This 670 cm$^{-1}$ melamine band was used to develop simple ratio algorithms for melamine detection. The results surprisingly revealed that the ratio algorithm could be used not only to perform the classification analysis between melamine uncontaminated and contaminated classes as low as the level of 0.2% (w/w), but also to predict the melamine concentrations in contaminated products. Notably, the algorithm approach is the most attractive and interesting since, in its simplest form, there is no calibration model which is commonly built from a large number sample set. In addition, the use of intensity ratios at different wavelengths can reduce the influences from diverse samples; hence it could be universally applied for fast, accurate, specific, and routine screening of melamine contaminant in unknown products. A Raman chemical imaging technique was applied to identify and image the melamine in a wheat flour matrix. Spectral imaging was demonstrated as a promising method of detection of intentional tainting of agricultural commodities that affects the safety and security of foods and feeds.

All of the references cited herein, including U.S. patents, are incorporated by reference in their entirety.

Thus, in view of the above, the present invention concerns (in part) the following:

A method for determining the presence of a contaminant in a sample comprising (or consisting essentially of or consisting of):

a) illuminating a sample with substantially monochromatic light to thereby produce Raman scattered photons;

b) collecting said Raman scattered photons to thereby generate Raman spectroscopic data wherein said Raman spectroscopic data comprises (or consists essentially of or consists of) at least one Raman spectrum representative of said sample;

c) analyzing said Raman spectroscopic data to thereby determine at least one of: the presence of a contaminant in said sample and the absence of a contaminant in said sample.

The above method wherein said contaminant comprises (or consists essentially of or consists of) melamine.

The above method wherein said contaminant is selected from the group consisting of: cyanuric acid, ammeline, ammelide, and combinations thereof.

The above method wherein said sample comprises at least one of: wheat flour, corn gluten, and soybean meal. The above method wherein said sample is selected from the group consisting of wheat flour, corn gluten, soybean meal, or mixtures thereof.

The above method wherein if said sample is determined to contain a contaminant, applying an algorithm to thereby determine the concentration of said contaminant that is present in said sample. The method wherein said concentration of said contaminant is at least 0.2% of the total weight of said sample.

The above method wherein said Raman spectrum comprises (or consists essentially of or consists of) a peak at approximately (about) 670 cm$^{-1}$.

The above method wherein said photons are passed through a filter. The method wherein said filter is an electronically tuned liquid crystal tunable filter.

The above method wherein said sample is illuminated using wide-field illumination.

The above method further comprising obtaining a spatially accurate wavelength resolved Raman image representative of said sample.

The above method further comprising analyzing said spatially accurate wavelength resolved Raman image to thereby determine at least one of: the presence of a contaminant in said sample and the absence of a contaminant in said sample. The method wherein if said s sample is determine to contain a contaminant, applying an algorithm to thereby determine the concentration of said contaminant present in said sample. The method wherein said concentration of said contaminant is at least 0.2% of the total weight of said sample.

The above method wherein said sample is illuminated using a (about) 1064 nm excitation laser.

The above method wherein said sample is illuminated using a (about) 785 nm excitation laser.

A method for determining the presence of a contaminant in a sample comprising (or consisting essentially of or consisting of)):

a) illuminating a sample with substantially monochromatic light to thereby produce Raman scattered photons;

b) collecting said Raman scattered photons to thereby generate Raman spectroscopic data wherein said Raman spectroscopic data comprises (or consists essentially of or consists of) at least one spatially accurate wavelength resolved Raman image representative of said sample;

c) analyzing said Raman spectroscopic data to thereby determine at least one of: the presence of a contaminant in said sample and the absence of a contaminant in said sample.

The above method wherein said contaminant comprises (or consists essentially of or consists of) melamine.

The above method wherein said contaminant is selected from the group consisting of: cyanuric acid, ammeline, ammelide, and combinations thereof.

The above method wherein said sample comprises (or consists essentially of or consists of) at least one of: wheat flour, corn gluten, and soybean meal. The method wherein said sample is selected from the group consisting of wheat flour, corn gluten, soybean meal, and mixtures thereof.

The above method wherein if said sample is determined to contain a contaminant, applying an algorithm to thereby determine the concentration of said contaminant that is present in said sample. The method wherein said concentration of said contaminant is at least 0.2% of the total weight of said sample.

The above method wherein said sample is illuminated using an illumination wavelength selected from the group consisting of approximately 785 nm, approximately 1064 nm, and combinations thereof.

The above method wherein said photons are passed through a filter. The method wherein said filter is an electronically tuned liquid crystal tunable filter.

The above method wherein said sample is illuminated using wide-field illumination.

The above method further comprising obtaining at least one Raman spectrum representative of said sample. The method further comprising analyzing said at least one Raman spectrum representative of said sample to thereby determine at least one of: the presence of said contaminant and the absence of said contaminant. The method wherein if said sample is determined to contain a contaminant, applying an algorithm to thereby determine the concentration of said contaminant that is present in said sample. The method wherein said concentration of said contaminant is at least 0.2% of the total weight of said sample.

The above method further comprising the steps of:

d) illuminating said sample with broadband light to thereby produce photons selected from the group consisting of: reflected by said sample, absorbed by said sample, transmitted by said sample, scattered by said sample, and combinations thereof;

e) collecting said photons to thereby generate at least one bright field image representative of said sample;

f) fusing said bright field image and said spatially accurate wavelength resolved Raman image to thereby identify at least one region of interest of said sample;

g) obtaining at least one Raman spectrum representative of said at least one region of interest;

h) analyzing said at least one Raman spectrum to thereby determine at least one of: the presence of a contaminant in said sample and the absence of said contaminant in said sample. The method wherein if said sample is determined to contain a contaminant, applying an algorithm to thereby determine the concentration of said contaminant that is present in said sample. The method wherein said concentration of said contaminant is at least 0.2% of the total weight of said sample.

The above method wherein said sample is illuminated using a (about) 1064 nm excitation laser.

The above method wherein said sample is illuminated using a (about) 785 nm excitation laser.

A method for determining the presence of a contaminant in a sample comprising (or consisting essentially of or consisting of):

a) illuminating a sample with a first illumination wavelength to thereby produce Raman scattered photons;

b) collecting said Raman scattered photons to thereby generate Raman spectroscopic data wherein said Raman spectroscopic data comprises (or consists essentially of or consists of) at least one Raman spectrum;

c) selecting a first Raman band of interest and a second Raman band of interest from said Raman spectrum;

c) obtaining a ratio of said first Raman band of interest and said second Raman band of interest;

d) obtaining a correlation coefficient of said ratio;

e) comparing said correlation coefficient to a predetermined threshold value wherein:

1. if said correlation coefficient is greater than said predetermined threshold value, confirming the presence of a contaminant in said sample, and
2. if said correlation coefficient is less than said predetermined threshold value, confirming the absence of a contaminant in said sample.

The above method wherein said contaminant comprises (or consists essentially of or consists of) melamine.

The above method wherein said contaminant is selected from the group consisting of cyanuric acid, ammeline, ammelide, and combinations thereof.

The above method wherein said sample comprises (or consists essentially of or consists of) at least one of: wheat flour, corn gluten, and soybean meal. The method wherein said sample is selected from the group consisting of wheat flour, corn gluten, soybean meal, and mixtures thereof.

The above method wherein if said sample is determined to contain a contaminant, applying an algorithm to thereby determine the concentration of said contaminant that is present in said sample. The method wherein said concentration of said contaminant is at least 0.2% of the total weight of said sample.

The above method wherein one of said first Raman bands of interest and said second Raman bands of interest is approximately 670 cm$^{-1}$.

The above method wherein at least one illumination of said sample is achieved using a (about) 1064 nm excitation laser.

The above method wherein at least one illumination of said sample is achieved using a 785 nm excitation laser.

A system for detecting the presence of a contaminant in a sample comprising (or consisting essentially of or consisting of):

a) an illumination source configured to illuminate a sample with substantially monochromatic light to thereby produce Raman scattered photons;

b) a detector for detecting said Raman scattered photons and generating Raman spectroscopic data representative of said sample;

c) a processor for processing said Raman spectroscopic data; and d) a display for displaying at least one of: a Raman spectrum representative of said sample and a spatially accurate wavelength resolved Raman image representative of said sample.

The above system wherein said illumination source is an excitation laser selected from the group consisting of: 785 nm, 1064 nm, and combinations thereof.

The above system further comprising an electronically tuned liquid crystal tunable filter.

The above system wherein said detector is a InGaAs detector.

The above system wherein said illumination source is a Nd:YAG excitation laser.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed is:

1. A method for determining the presence of a contaminant in a sample comprising:
    a) illuminating a non-aqueous macroscopic sample using wide-field illumination in which a field of view to be investigated is illuminated with substantially monochromatic light to thereby produce Raman scattered photons;
    b) collecting said Raman scattered photons to thereby generate Raman spectroscopic data wherein said Raman spectroscopic data comprises at least one Raman image representative of said sample, said at least one Raman image comprising a non-microscopic Raman chemical image comprising at least one Raman spectrum;
    c) analyzing said Raman chemical image to thereby determine at least one of: the presence of a contaminant in said sample and the absence of a contaminant in said sample.

2. The method of claim 1 wherein said contaminant comprises melamine.

3. The method of claim 1 wherein said contaminant is selected from the group consisting of: cyanuric acid, ammeline, ammelide, and combinations thereof.

4. The method of claim 1 wherein said sample comprises at least one of: wheat flour, corn gluten, and soybean meal.

5. The method of claim 1, further applying an algorithm to thereby determine a concentration of said contaminant that is present in the sample.

6. The method of claim 5 wherein said concentration of said contaminant is at least 0.2% of the total weight of said sample.

7. The method of claim 1 wherein said Raman spectrum comprises a peak at approximately 670 cm$^{-1}$.

8. The method of claim 1 wherein said photons are passed through a filter.

9. The method of claim 8 wherein said filter is an electronically tuned liquid crystal tunable filter.

10. The method of claim 1 wherein said sample is illuminated using a 1064 nm excitation laser.

11. The method of claim 1 wherein said sample is illuminated using a 785 nm excitation laser.

12. The method of claim 1 wherein the sample comprises a heterogeneous sample.

13. A method for determining the presence of a contaminant in a sample comprising:
   a) illuminating a non-aqueous macroscopic sample using wide-field illumination in which a field of view to be investigated is illuminated with substantially monochromatic light to thereby produce Raman scattered photons;
   b) collecting said Raman scattered photons to thereby generate Raman spectroscopic data wherein said Raman spectroscopic data comprises at least one spatially accurate wavelength resolved non-microscopic Raman chemical image representative of said sample;
   c) analyzing said Raman chemical image to thereby determine at least one of: the presence of a contaminant in said sample and the absence of a contaminant in said sample.

14. The method of claim 13 wherein said contaminant comprises melamine.

15. The method of claim 13 wherein said contaminant is selected from the group consisting of: cyanuric acid, ammeline, ammelide, and combinations thereof.

16. The method of claim 13 wherein said sample comprises at least one of: wheat flour, corn gluten, and soybean meal.

17. The method of claim 13, further applying an algorithm to thereby determine a concentration of said contaminant that is present in the sample.

18. The method of claim 17 wherein said concentration of said contaminant is at least 0.2% of the total weight of said sample.

19. The method of claim 13 wherein said sample is illuminated using an illumination wavelength selected from the group consisting of: approximately 785 nm, approximately 1064 nm, and combinations thereof.

20. The method of claim 13 wherein said photons are passed through a filter.

21. The method of claim 20 wherein said filter is an electronically tuned liquid crystal tunable filter.

22. The method of claim 13 further comprising obtaining at least one Raman spectrum representative of said sample.

23. The method of claim 22 further comprising analyzing said at least one Raman spectrum representative of said sample to thereby determine at least one of: the presence of said contaminant and the absence of said contaminant.

24. The method of claim 22, further applying an algorithm to thereby determine a concentration of said contaminant that is present in the sample.

25. The method of claim 24 wherein said concentration of said contaminant is at least 0.2% of the total weight of said sample.

26. The method of claim 13 further comprising the steps of:
   d) illuminating said sample with broadband light to thereby produce photons selected from the group consisting of: reflected by said sample, absorbed by said sample, transmitted by said sample, scattered by said sample, and combinations thereof;
   e) collecting said photons to thereby generate at least one bright field image representative of said sample;
   f) fusing said bright field image and said spatially accurate wavelength resolved Raman image to thereby identify at least one region of interest of said sample;
   g) obtaining at least one Raman spectrum representative of said at least one region of interest;
   h) analyzing said at least one Raman spectrum to thereby determine at least one of: the presence of a contaminant in said sample and the absence of a contaminant in said sample.

27. The method of claim 26, further applying an algorithm to thereby determine a concentration of said contaminant that is present in the sample.

28. The method of claim 27 wherein said concentration of said contaminant is at least 0.2% of the total weight of said sample.

29. The method of claim 13 wherein said sample is illuminated using a 1064 nm excitation laser.

30. The method of claim 13 wherein said sample is illuminated using a 785 nm excitation laser.

* * * * *